United States Patent [19]
Elnagar

[11] Patent Number: 6,103,926
[45] Date of Patent: Aug. 15, 2000

[54] BENZYLIC HALOGENATION OF ALKYLBENZOIC ACID ESTERS

[75] Inventor: Hassan Y. Elnagar, Baton Rouge, La.

[73] Assignee: Albemarle Corporation, Richmond, Va.

[21] Appl. No.: 09/266,879

[22] Filed: Mar. 12, 1999

[51] Int. Cl.$^7$ .................................................. C07C 69/76
[52] U.S. Cl. .......................................................... 560/103
[58] Field of Search ............................................. 560/103

[56] References Cited

FOREIGN PATENT DOCUMENTS 44-28699  11/1969  Japan .

OTHER PUBLICATIONS

Listvan, V.N. et al., "Reactions of Phosphorus Ylides with Acylating Agent in a Two–Phase System", J. Gen. Chem., USSR, 1987, vol. 57, pp. 1366–1371 (English Translation).
Mamalis, P. et al., "Amino–oxy–derivatives. Part V. Some O–Ethers of 2–Substituted 4,6–Diamino–1, 2–dihydro–1–hydroxy–1,3,5–triazines", J. Chem. Soc., 1965, pp. 1829–1843.
King, F.E. et al., "The Constitution of Chlorophorin. Part II. Further Oxidation Experiments, and the Completion of the Structural Problem.", J. Chem. Soc., 1950, pp. 3547–3552.
Barany, George et al., "A Three–Dimensional Orthogonal Protection Scheme for Solid–Phase Peptide Synthesis under Mild Conditions", J. Am. Chem. Soc., 1985, vol. 107, pp. 4936–4942.
Marvel, C.S. et al., "Polythiolesters. II. Preparation In Emulsions", J. Org. Chem., 1953, pp. 707–714.
Titley, A. F., "Conditions of Formation of Rings attached to the o–, m–, and p–Positions of the Benzene Nucleus. Part III.", J. Chem. Soc. 1928, pp. 2571–2583.
Codington, John F. et al., "Reactions with 4'–Carboxy–4–Chlorostilbene", J. Org. Chem., 1952, pp. 1035–1042.
Houlihan et al., "Antitumor Activity of 5–Aryl–2,3–dihydroimidazo[2,1–60 ]isoquinolines", J. Med. Chem., 1995, vol. 38, pp. 234–240.
Chaintreau et al., "Cupric Bromide As Benzylic Bromination Reagent In Polar Media", Synth. Commun., 1981, vol. 11, No. 8, pp. 669–672.

*Primary Examiner*—Paul J. Killos
*Attorney, Agent, or Firm*—E. E. Spielman, Jr.

[57] ABSTRACT

Direct preparation of benzylically halogenated alkylbenzoic acid ester from an alkylbenzoic acid ester in which the alkyl group is a primary or secondary alkyl group is carried out. The ester group of the starting ester (i) is devoid of non-aromatic unsaturation and (ii) if an aromatic group, is devoid of ring substitution that would undergo benzylic halogenation. The process comprises slowly feeding halogen continuously and/or intermittently to an agitated solution of the alkylbenzoic acid ester in a liquid halogen-containing solvent maintained at a thermal halogenation temperature such that when the alkyl group of the alkylbenzoic acid ester is a primary alkyl group and monohalogenation is desired, the total amount of halogen fed does not exceed about 0.8 mole of halogen per mole of alkylbenzoic acid ester. If the alkylbenzoic acid ester is a toluic acid ester and dihalogenation is desired, the amount of halogen fed is over 1 mole but no more than about 1.8 moles per mole of the toluic acid ester. Ester cleavage is minimized and other advantages are made possible.

30 Claims, No Drawings

BENZYLIC HALOGENATION OF ALKYLBENZOIC ACID ESTERS

TECHNICAL FIELD

This invention relates generally to the direct synthesis of mono- and dihaloalkylbenzoic acid esters from alkylbenzoic acid esters, and especially to the direct synthesis of monobromoalkylbenzoic acid esters, such as methyl or ethyl 4-(bromomethyl)benzoate (a.k.a. methyl or ethyl p-toluate) from methyl or ethyl p-toluate.

BACKGROUND

Haloalkylbenzoic acid esters having one or two halogen atoms on the alpha-carbon atom of the alkyl group are useful as chemical intermediates. For example, alkyl esters of 4-(bromomethyl)-benzoate such as the methyl or ethyl ester, are useful as intermediates in the synthesis of Eprosartan, (SKF-108566), a prototype of imidazoleacrylic acid angiotensin II receptor antagonists.

Few examples of radical bromination of p-toluic acid and its methyl and ethyl esters have appeared in the literature. See in this connection:

Listvan, V. N.; Stasyuk, A. P.; Kurgan, L. N., *J. Gen. Chem. USSR*, 1987, vol. 57, 1366 (English Translation);

Chaintreau, A.; Adrian, G.; Coutrier, D., *Synth. Commun.*, 1981, 11, 669;

Houlihan, W. J.; Munder, P. G.; Handley, D. A.; Cheon, S. H.; Parrino, V. A., *J. Med. Chem.*, 1995, 38, 234;

Mamalis, P.; Green, J.; Outred, D. J.; Rix, M. J., *J. Chem. Soc.*, 1965, 1829;

King, F. E.; Grudon, M. F., *J. Chem. Soc.*, 1950, 3547;

Barany, G.; Albericio, F., *J. Am. Chem. Soc.*, 1985, 107, 4936; and

Marvel, C. S.; Kraiman, E. A., *J. Org. Chem.*, 1953, 707.

In all of these prior processes, the bromination was carried out photochemically or by use of N-bromosuccinimide (NBS) or other bromine compound such as $CuBr_2$. Only a single reference where bromine was used as bromination reagent to prepare ethyl 4-(bromomethyl)benzoate appeared some 70 years ago, and this involved an indirect two-step synthesis. Thus, Titley, A. F., *J. Chem. Soc.*, 1928, 2571, describes treatment of p-toluolyl acid halides with bromine, followed by treatment with ethanol. p-Toluic acid itself was reportedly brominated at the benzylic position by bromine in nitrobenzene in 50% yield (Codington, J. F.; Mosettig, E., *J. Org. Chem.*, 1952, 1035). No reference was found where the methyl or ethyl esters of p-toluic acid were directly converted to the corresponding benzylbromide by elemental bromine.

It was found possible in our laboratories to produce the methyl and ethyl esters of 4-(bromomethyl)benzoic acid photochemically using a sun lamp and bromine, and/or bromine/hydrogen peroxide in halogenated solvents in the presence of water. The product was recovered by recrystallization from aqueous ethanol or 2-propanol. This, however, is not a commercially viable process for operation on an industrial scale. Likewise, brominations using bromine compounds such as NBS or dibromodimethylhydantoin (DBDMH) suffer not only from the relatively high cost of the bromine sources, but from the formation of organic waste composed of coproduct amides.

A process enabling direct production of methyl or ethyl 4-(bromomethyl)benzoate in one step and in good yield by bromination of the ester of p-toluic acid with bromine would be commercially desirable. It was found, however, from attempts to carry out such direct bromination that there is a complicating factor—that of the tendency for the bromine to cause ester cleavage under thermal bromination conditions.

A need exists for an effective process enabling the direct one-step synthesis of mono- and dihaloalkylbenzoic acid esters with the halogen atom(s) on the alpha-carbon atom of the alkyl group, using bromine and a primary alkylbenzoic acid ester as the reactants. Such a process, if attainable, would avoid the shortcomings noted above.

This invention is deemed to have fulfilled this need.

SUMMARY OF THE INVENTION

This invention makes it possible to carry out the thermal benzylic halogenation of primary or secondary alkylbenzoic acid esters using elemental halogen such as chlorine or, preferably, bromine, to produce the corresponding benzylically brominated ester. The desired product can be produced in good yield in a one-step synthesis. Ester cleavage during halogenation is minimized. Moreover, the thermal halogenation process is insensitive to impurities often present in starting toluate esters such as p-toluic acid or its salts. And the only appreciable co-product formed is hydrogen halide, materials which can readily be recovered, and converted to or used in the synthesis of other products. Thus, problems associated with waste product formation and disposal are minimized.

One of the embodiments of this invention is a process for the direct preparation of a (1-haloalkyl)benzoic acid ester from an alkylbenzoic acid ester in which the alkyl group is a primary or secondary alkyl group and wherein the ester group (i) is devoid of non-aromatic unsaturation and (ii) if an aromatic group, is devoid of ring substitution that would undergo benzylic halogenation, which process comprises slowly feeding halogen continuously and/or intermittently to an agitated solution of the alkylbenzoic acid ester in a liquid halogen-containing solvent maintained at a thermal halogenation temperature such that when the alkyl group of the alkylbenzoic acid ester is a primary alkyl group the total amount of halogen fed does not exceed about 0.8 mole of halogen per mole of alkylbenzoic acid ester.

In one of the preferred forms of the above embodiment a (monobromomethyl)benzoate ester is prepared from a toluic acid ester in which the ester group is (i) devoid of non-aromatic unsaturation and (ii) if an aromatic group, is devoid of ring substitution that would undergo benzylic bromination. Here bromine is used in the process, and the reactant proportions are controlled such that the total amount of bromine fed does not exceed about 0.8 mole of bromine per mole of toluic acid ester.

It is also deemed possible to directly prepare a (1,1-dihaloalkyl)benzoic acid ester from an alkylbenzoic acid ester in which the alkyl group is a primary alkyl group having at least 2 carbon atoms and wherein the ester group is devoid of non-aromatic unsaturation. In this case the halogen is slowly fed continuously and/or intermittently to an agitated solution of the alkylbenzoic acid ester in a liquid halogen-containing solvent maintained at a thermal halogenation temperature such that the total amount of halogen fed is in excess of 1 mole of halogen per mole of alkylbenzoic acid ester.

Another possibility is the preparation of a (1,1-dihalomethyl)benzoic acid ester from a toluic acid ester in which the ester group (i) is devoid of non-aromatic unsaturation and (ii) if an aromatic group is devoid of ring substitution that would undergo benzylic halogenation. This process comprises slowly feeding halogen continuously and/or intermittently to an agitated solution of the toluic acid ester in a liquid halogen-containing solvent maintained at a thermal halogenation temperature such that the total amount of halogen fed is in the range of more than 1 mole but less than about 1.8 moles of halogen per mole of toluic acid ester.

Benzylic thermal halogenation pursuant to this invention is an uncatalyzed, non-photochemical bromination which can be conducted as a batch process, as a semi-continuous process, or as a continuous process.

The above and other embodiments and features of this invention will be still further apparent from the ensuing description and appended claims.

FURTHER DETAILED DESCRIPTION

Since the process of this invention involves bromination, the ester group of the alkylbenzoic acid ester will typically be devoid of non-aromatic unsaturation, as the presence of olefinic or acetylenic unsaturation in the ester group would constitute another site for bromination to occur. However if one desires to produce a compound such as the 1,2-dibromopropyl ester of (1-bromomethyl)-p-toluic acid, the allyl ester of p-toluic acid can be brominated in accordance with this invention. Likewise if the esterifying group is an aryl group, it is preferable that the aryl group be devoid of substitution thereon that is susceptible to benzylic halogenation, unless of course it is desired to produce a product in which halogenation occurs both on the alkyl group of the benzoic acid group and also on the substituent group(s) of the aryl esterifying group as well.

The alkyl group of the alkylbenzoic acid ester can be in the ortho-, meta-, or para-position relative to the carboxylic ester functionality. Of these, the p-alkylbenzoic acid esters are preferred. The alkyl group itself must contain at least one hydrogen atom on the alpha-carbon atom, and thus the alkyl group is a primary or secondary alkyl group, and preferably is a primary alkyl group. Typically it will contain no more than about 12 carbon atoms, but this is not a requirement. Any primary or secondary alkyl group capable of benzylic halogenation can be the alkyl group of the alkylbenzoic acid ester provided only that the ester will be at least partially dissolved in the halogen-containing solvent at the thermal halogenation temperature being used. Preferred alkylbenzoic acid esters are o-toluic acid esters, m-toluic acid esters, and especially p-toluic acid esters of the formula $CH_3$—$C_6H_4$—COOR in which R is a hydrocarbyl group that is (i) devoid of non-aromatic unsaturation, (ii) that contains no more than about 12 carbon atoms, and (iii) that is itself not susceptible to benzylic halogenation. Use of such reactants tends to provide a clean-cut reaction. However, as noted above, it is within the scope of this invention for R to contain non-aromatic unsaturation (which will undergo halogenation during the thermal halogenation) and/or to be an aryl group such as a tolyl or xylyl group that is itself susceptible to benzylic halogenation, when such additional halogenation is desired in the end product of the reaction. The amount of halogen used in such cases should of course be proportionately increased to take into consideration the amount of halogen that will be consumed in halogenating the non-aromatic unsubstitution and/or the aryl substituent group(s) susceptible to benzylic halogenation.

A few non-limiting illustrative examples of alkylbenzoic acid esters that can be used in the practice of this invention include methyl o-toluate, methyl m-toluate, methyl p-propylbenzoate, methyl p-isopropylbenzoate, butyl p-toluate, ethyl p-sec-butylbenzoate, phenyl m-n-octylbenzoate, cyclohexyl n-butylbenzoate, p-(tert-butyl) phenyl p-n-decylbenzoate, 4-biphenylyl p-toluate, and analogous primary or secondary alkylbenzoic acid esters. Particularly preferred alkylbenzoic acid esters are methyl p-toluate and ethyl p-toluate.

The halogen used in the practice of this invention should be of commercial purity. It can be charged to the reaction mixture in neat liquid form if the reaction mixture is being well-agitated so that the halogen is almost immediately thoroughly dispersed in the reaction mixture. The objective of such mixing is to avoid, or at least to minimize, the existence of localized concentrations or accumulations of free halogen in the reaction mixture, as such localized concentrations or accumulations of free halogen can cause cleavage of the ester reactant and of the corresponding halogenated benzyl ester being produced. Typically the halogen used will be chlorine or bromine, with bromine being the preferred reactant. To assist in the rapid dispersal of bromine in the agitated reaction mixture and to reduce the possibility of localized concentrations or accumulations of bromine being formed in the reaction mixture, it is preferred to feed bromine either as a solution in a suitable halogenated solvent, most preferably the same solvent that was used in forming the reaction mixture, or to feed the bromine in the form of a vaporous mixture diluted with an inert gas such as nitrogen, argon, neon, or krypton. In addition, it has been found that premixing of bromine and an inert gas such as nitrogen can result in reaction rate acceleration and minimization of benzal byproduct formation in the synthesis of methyl (1-bromomethyl)benzoate.

Suitable halogen-containing solvents for use in the process are halogen-containing solvents devoid of non-aromatic unsaturation and substitution susceptible to benzylic halogenation. Thus use can be made of saturated haloaliphatic compounds, saturated halocycloaliphatic compounds, and haloaromatic compounds that are in the liquid state of aggregation at least over the range of temperatures from, say, 20° C. to at least the bromination temperature being used. To avoid product contamination, the halogen of the solvent should not be susceptible to displacement by the halogen reactant being used. Thus when using bromine, the solvent should be iodine-free. If chlorine is used, the solvent should be a chlorine-containing and/or fluorine-containing solvent. The solvent should have a boiling temperature below that of the benzylically halogenated alkylbenzoate ester being produced, and preferably no higher than about 160° C. so that the solvent can be distilled away from the desired product without need for prolonged heating at elevated temperatures. Prolonged exposure of the product to elevated temperatures can be detrimental because benzylic halides are generally thermally labile. A few examples of suitable solvents include 1-bromopentane (bp 128–129° C.), 1-chlorohexane (bp 132° C.), 2-chlorohexane (bp 123° C.), 1,1-dibromoethane (bp 110° C.), 1,3-dichloropropane (bp 120–122° C.), perfluorononane (bp 125–126° C.), cyclopentylbromide (bp 137–139° C.), 1,2-dibromopropane (bp 140–142° C.), bromobenzene (bp 156° C.), 1-bromohexane (bp 156° C.), and similar solvents. When producing methyl or ethyl (1-bromomethyl)benzoate the solvent preferably has a boiling temperature in the range of about 130 to about 150° C., and particularly preferred materials of this type are chlorobenzene (bp 132° C.) and 1,2-dibromoethane (bp 131–132° C.). Solvents having boiling temperatures near the upper ends of the foregoing ranges can be distilled away from the product at reduced pressures, and such vacuum distillation can be advantageous in minimizing the extent to which the product is exposed to elevated temperatures.

To increase reactor loading and to minimize the time during which the final product is exposed to distillation temperatures during product recovery, it is desirable to avoid use of excessively dilute reaction mixtures. Conversely, the amount of the solvent should be sufficient to dissolve the ester reactant and to keep the brominated product in solution during the reaction. Also it has been found that at least in the case of bromination of the methyl ester of p-toluic acid, the presence of an insufficient amount of solvent can lead to extensive ester cleavage. Therefore to minimize the extent of ester cleavage, the thermal halogenation reaction should be performed in an amount of solvent that suppresses ester cleavage, if any, to an acceptable level. The conditions can also have an effect upon the amount of ester cleavage. For example, the results of laboratory experiments indicate that the amount of cleavage when stirring the reaction mixture at 400 rpm was less than the amount observed at 300 rpm. Likewise the dilution of bromine with nitrogen prior to feed to the reaction mixture reduced the amount of ester cleavage as compared to the feed of undiluted bromine. Thus, in general, it is apparent that the extent of ester cleavage, if any, encountered during the thermal halogenation reaction is influenced by a combination of factors such as (i) the amount of solvent relative to the amount of alkylbenzoic ester reactant charged to the reactor, (ii) the rate of agitation or mixing of the reactants during the reaction, and (iii) the extent to which, if at all, the halogen is diluted prior to introduction into the reaction mixture. The temperature and the identities of the halogen and the ester being halogenated may also have an influence of ester cleavage, if any. Therefore, at present there is no set of conditions that can be said to be universally applicable for minimizing or totally eliminating ester cleavage of all esters with any halogen under all temperature conditions with all solvents. Moreover, the amount of cleavage (where there is cleavage) that is acceptable for one synthesis may not be acceptable for another, and the amount of cleavage (where there is cleavage) that is acceptable to one manufacturer for a given synthesis may not be acceptable to another manufacturer conducting the same synthesis. These matters are necessarily subjective as they involve such factors as economics and profit margins, separation facilities available for use, usage for which the end product is intended, and so on. Thus in any given situation where optimization is desired to minimize or totally eliminate ester cleavage (if cleavage is experienced on the first try), a few pilot laboratory experiments should be performed using the guidelines presented herein to achieve such optimization. There is at present no reason to believe that where ester cleavage is encountered, it cannot be eliminated, or at least reduced, by application of the above principles such that less than 5 grams (preferably less than 3 grams) of free benzoic acid(s) are formed per each 150 grams of ester being subjected to halogenation pursuant to this invention.

In general, the solvent and the initial alkylbenzoic acid ester will typically be proportioned such that there are in the range of about 0.4 to about 1.5 parts by weight of the solvent, and preferably in the range of about 0.7 to about 1.1 parts by weight of the solvent per each part by weight of the alkylbenzoic acid ester charged to the reactor. Most preferably, the weight ratio of the solvent to the alkylbenzoic acid ester is about 1:1. The alkylbenzoic acid ester and the solvent can be separately charged to the reactor concurrently or sequentially in any order, or they can be premixed and fed as a solution. The halogen feed should not be initiated unless the reactor contains enough of the ester reactant and solvent, proportioned as just described, that will maintain at all times a stoichiometric excess of the ester relative to the halogen. If this caveat is observed, co-feeding of (i) the bromine and (ii) the ester and solvent, whether premixed or fed individually, can be utilized. In conducting such co-feeding, the feeds (i) and (ii) occur concurrently for at least some portion of time, but not necessarily at all times. Preferably, the feed of (ii) is initiated before the feed of (i), and thereafter concurrent feeding, whether either or both of (i) and (ii) are continuous or intermittent, will take place until the requisite amounts have been fed or until the continuous or semi-continuous operation is shut down.

As noted above, the halogen is slowly fed continuously and/or intermittently to an agitated solution of the alkylbenzoic acid ester in a liquid halogen-containing solvent maintained at a thermal halogenation temperature. By "slowly" is meant that with a reaction mixture that is being thoroughly agitated (stirred or otherwise mixed), the addition of the halogen should be slow enough that a dark or pronounced coloration should not be visually observable to the naked eye. For example, when using bromine, the feed should be slow enough that the dark bromine color does not appear in the agitated reaction mixture. Also at least when producing the methyl or ethyl ester of (4-bromomethyl)benzoate, the rate of bromine addition should be slow enough that no solids formation in the reaction mixture can be seen by the naked eye. As a general rule, the faster the agitation and the higher the temperature, the faster the halogen can be fed.

Also noted above is the fact that the total amount of halogen fed depends upon the type of product being produced and the type of ester being halogenated. Thus when producing via benzylic halogenation an ester of a monohaloalkylbenzoic acid ester the mole ratio of diatomic halogen ($X_2$) to primary alkylbenzoic acid ester should not exceed about 0.8. While the desired product will still be formed at ratios somewhat above about 0.8, the amounts of higher brominated byproducts increase with increased ratios. For the same reason, to prepare a (1,1-dihalomethyl)benzoic acid ester from a toluic acid ester, the mole ratio of diatomic halogen to the toluic acid ester should not exceed about 1.8. When producing via benzylic halogenation an ester of a monohaloalkylbenzoic acid ester from a secondary alkylbenzoic acid ester, the mole ratio of diatomic halogen ($X_2$) to secondary alkylbenzoic acid ester can be up to, and preferably is, approximately 1:1, although in many cases excess bromine can be used if desired.

The thermal halogenation is conducted at an elevated temperature at which the benzylic halogenation occurs, and at which no thermal decomposition of any component in the reaction mixture occurs. The reaction can be performed at a suitable temperature below the boiling temperature of the halogen-containing solvent, or the reactor may be equipped with a reflux condenser so that the reaction can be performed under reflux conditions. In either case the hydrogen halide is removed from the reactor and can be neutralized in a caustic scrubber, or recovered in gaseous form or as the aqueous acid. Typically the temperature at which the thermal halogenation is performed will be in the range of about 100 to about 160° C., preferably in the range of about 110 to about 150° C., and more preferably in the range of about 135 to about 145° C. The reaction can be performed at atmospheric pressure, or at reduced or elevated pressures. If desired, the pressure and/or the temperature can be varied during the course of the halogenation reaction.

To produce high quality product with no color formation, residual hydrogen halide such as HBr should be removed from the reaction mixture. One way of removing residual hydrogen halide is to wash the reaction mixture with water.

Another way of removing residual hydrogen halide is to purge the reaction mixture with an inert gas at the end of the halogen addition, especially if the purging operation is performed with the reaction mixture at an elevated temperature. It has been found, for example, that purging with nitrogen with the temperature above about 100° C. removed most residual hydrogen bromide from a reaction mixture in which chlorobenzene was the solvent. However, residual amounts of HBr in the order of about 1 wt % were detected in the chlorobenzene solution after such nitrogen purge. The combination of an inert gas purge followed by water washing is still another way of removing residual amounts of hydrogen halide from the reaction mixture. In situations where complete or substantially complete removal of residual hydrogen halide is to be effected, recourse to at least one or more water washings is recommended, preceded if desired by a purge with nitrogen or other inert gas.

The halogenation of primary alkylbenzoic acid esters to produce monohaloalkylbenzoic acid esters is best conducted at conversions no higher than about 80 mole % based on the amount of ester employed, and the halogen should be fed slowly to the reaction mixture. Similarly, the halogenation of methylbenzoic acid esters to produce dihalomethylbenzoic acid esters is best conducted at conversions no higher than about 90 mole % based on the amount of ester employed, and here again the halogen should be fed slowly to the reaction mixture. High conversion operation and fast halogen addition, while operable, lead to ester cleavage and carboxylic acid formation, and consequent need for additional product purification in order to obtain a high purity product. Thus operation at high conversion with fast halogen addition are not preferred, except in situations where product purity is of no concern or where subsequent purification to remove organic byproducts forms part of the overall operation. To illustrate, if the conditions used in the bromination of a 4-methylbenzoic acid ester are selected such that cleavage occurs resulting in formation of 4-monobromomethylbenzoic acid and p-toluic acid byproducts, the former byproduct is almost completely insoluble in chlorobenzene, whereas the latter byproduct is only partially soluble in chlorobenzene. Thus these byproducts can be largely removed by filtration or more completely by washing with an aqueous alkali metal carbonate (e.g., aqueous $Na_2CO_3$ or $K_2CO_3$), or alkali metal hydroxide solution (e.g., aqueous NaOH or KOH). In many cases, vacuum distillation can be employed to produce a highly purified product.

The following Examples are presented for purposes of illustration. They are not intended to constitute, and should not be construed as constituting, limitations on the scope of this invention.

In the following Examples the experimental protocol was as follows: Thermal bromination was carried out in glass round bottomed flask. The flask is typically dyed with Amber Stain # 657, American Ceramic Laboratories Inc. The reaction flask was equipped with a sealed mechanical stirrer and fitted with a reflux condenser. The whole assembly was wrapped with aluminum foil to minimize possible light interference. Bromine was charged into a graduated cylinder and fed to the reactor via a Masterflex computerized Drive pump. Liquid bromine was transferred using Viton tubing L/S 14 used with Easy-Load Masterflex L/S head model 7518-10. Prior to addition, if desired, the bromine was premixed with nitrogen in a T-shaped Teflon tube. The bromination reaction mixture was heated by means of heating mantle. The heating mantle was connected to a temperature controller (J-KEM Electronics, Inc., Gemini-2 model) and set at the desired reaction temperatures (typically between 130 and 140° C.). Progress of the bromination reaction was monitored by Gas Chromatography. The analyses were conducted using an HP 5890A Gas Chromatograph using HP-1 column (Phase: SE-30, 15 meter, ID: 0.54 mm, Thickness: 1.2 micron, initial temperature 30° C., final temperature 260° C., rate 7° C./min).

Examples 1 and 2 illustrate brominations conducted pursuant to this invention.

EXAMPLE 1

Preparation of Ethyl 4-(Bromomethyl)benzoate (EBMB)

An ethyl 4-methylbenzoate (EMB) solution (1134 g in chlorobenzene (CB), ~43 wt. %, 2.93 mol) was charged into a 2-Liter round bottomed flask equipped with mechanical stirrer (300 RPM stirring rate) and a cooling condenser, and heated. The temperature controller was set at 140° C., and a scrubber was connected to the condenser. Liquid bromine (275 g, 1.72 mol or ~59 mol %, Aldrich, 99.5+%, A.C.S. reagent) was fed via Viton tubings, and the bromine feed rate was adjusted to 1.00 mL/minute for the first 30 mol % of bromine and then to 0.50 mL/minute for the rest of the addition at 140° C. Heating and stirring was continued for a few minutes after all bromine was added and the hot mixture was purged with nitrogen for 20 minutes, then allowed to cool to obtain 1183 g crude reaction mixture (some materials were used for routine analysis). The GC wt. % analysis of the crude reaction mixture indicated the following:

17.2% Starting EMB (Theoretical=203.6 g)

28.0% EBMB (Theoretical=331.5 g)

Distillation under reduced pressure removed first the solvent (CB), then the unreacted starting material (EMB, total of 192.6 g, ~95% of theoretical @ 19 Torr, 120° C.) as colorless oil. Next, the desired EBMB was recovered (283.3 g, ~86% of theoretical) at 18 Torr, 174° C., obtained as colorless low melting solid.

EXAMPLE 2

Preparation of Methyl 4-(Bromomethyl)benzoate (MBMB)

A methyl 4-methylbenzoate (MMB) solution (110 g, 0.73 mol) in CB (150 g) in a 250 mL round bottomed flask was heated by a heating mantle connected to a temperature controller to temperatures between 136 to 140° C. Liquid bromine (84.4 g, 0.53 mol or ~72 mol %), (Aldrich, 99.5+%, A.C.S. reagent) was fed via Viton tubings using Cole-Parmer computerized Drive with Easy-Load pump head. The bromine feed rate was adjusted to 0.50 mL/minute throughout the 52 minutes of addition time. Heating and stirring were continued for a few minutes after all bromine had been added, and then the reaction mixture was allowed to cool down. The "smoking" orange mixture was transferred to a separatory funnel and was washed with water (250 mL) to produce a colorless organic phase. The bottom layer (organic) was separated and concentrated under reduced pressure (rotary evaporator) to remove most of the chlorobenzene. The residual oily mixture was allowed to stand overnight. An impure crystalline solid was obtained. The crude solid was dissolved in 20% aqueous ethanol solution (450 mL) and allowed to cool in a refrigerator for 2 hours. The resulting white crystals were washed with 50% aqueous ethanol (200 mL) to produce 50.5 g (42% based on added bromine) of highly pure (~99%) material. No attempt was made to optimize the recovered yield.

EXAMPLE 3

To assess the effect of the magnitude of conversion on thermal bromination of the ethyl toluate by bromine, the ratio of the desired benzylbromide to the benzal bromide byproduct was examined as a function of added bromine. This was done by treating 164.5 g (1.0 mol) of ethyl 4-methylbenzoate in chlorobenzene (164.5 g) with liquid bromine at 145° C. The bromine was added at 0.5 mL/minute rate and the mixture was stirred at 300 rpm mixing rate. A trace of benzotribromide (three Br atoms at the benzylic position) was only detected near the end of the bromine addition. The reaction progress is summarized below in Table 1. The benzyl/benzal ratio decreased faster after ~50 mol % bromine was added.

TABLE 1

Conversion* of EMB vs. Selectivity: Bromination of EMB in PhCl.

| | | Normalized GC Area % | | | Selectivity | |
|---|---|---|---|---|---|---|
| $Br_2$ mol % | $Br_2$ wt.(g) | EMB | EBMB | Benzal | Benzyl/Benzal | Comments |
| 49.3 | 78.9 | 63.5 | 34.9 | 1.6 | 21.7 | |
| 68.9 | 110.1 | 43.5 | 52.3 | 4.2 | 12.5 | |
| 88.9 | 142.1 | 26.5 | 64.6 | 8.8 | 7.3 | Trace benzo-$Br_3$ |

*Addition of total 1.1 mol bromine (110 mol %) did not cause total conversion, but rather the added bromine converted the EBMB (product) to the benzal byproduct and the benzyl/benzal ratio decreased to 4.4. Then when the reaction mixture was allowed to cool down a solid precipitated. This solid was identified by GC/MS as the benzylbromide of toluic acid (6.2 g). It apparently resulted from increased HBr solubility due to presence of excess bromine (and reduced EMB concentration) and was formed by dealkylation of EBMB. Therefore, when preparing a monobromoalkylbenzoic acid ester from a primary alkylbenzoic acid ester such as EMB or MMB, excess bromine is detrimental to selectivity as well as to yields, particularly near the end of reaction.

EXAMPLE 4

Tables 2–4 (entries 1–11) summarize the results of experimental runs in which the bromination was carried out using 1.0 mole of MMB in CB solvent, and typically involved treated the same with ~0.75 mole of bromine. The MMB/CB ratio refers to relative weights.

TABLE 2

Effect of Concentration
(Solvent/Substrate wt. % Ratio) on the Ester Cleavage
During Thermal Bromination
(~75 mol % $Br_2$) of MMB in Chlorobenzene (CB)

| Entry | MMB:CB | Temp (C.) | $Br_2$ rate & mol. % | Isolated acids (g) | Comments |
|---|---|---|---|---|---|
| 1. | 1.0:1.36 | 136–140 | 0.50 72 | Trace | 300 rpm |
| 2. | 1.0:1.33 | 145 | 0.50 75 | Trace | 400 rpm |
| 3. | 1.0:1.33 | 145 | 0.25 75 | Trace | 400 rpm |
| 4. | 1.0:1.33 | 127-131 | 0.50 75 | 9.7 g | poor mix* |

Starting material, MMB = 150 g (1.0 mol). The term "isolated acids" refers to both p-toluic acid (PTA) and α-bromo-p-toluic acid (BPTA) formed- in a solid form -as a result demethylation of the ester group. The PTA is sparingly soluble in chlorobenzene especially at low temperature. The α-bromo-p-toluic acid is almost insoluble in CB. Liquid $Br_2$ feed rate is in ml/min.
*Many interruptions in mixing were due to mechanical problems. Bromine was visibly accumulated in the reaction mixture.

TABLE 3

Effect of Concentration
(Solvent/Substrate wt. % Ratio) & Nitrogen mixing
on Thermal Bromination (~75 mol % $Br_2$) of MMB in CB.

| Entry | MMB:CB | Temp (C.) | $Br_2$ rate & mol. % | Isolated acids (g) | Comments |
|---|---|---|---|---|---|
| 5. | 1.0:0.67 | 145 | 0.50 75 | 2.7 g | $N_2$ |
| 6. | 1.0:0.67 | 127–130 | 0.50 75 | 30.5 g | |
| 7. | 1.0:0.67 | 145 | 0.50 75 | 1.2 g | 400 rpm |
| 8. | 1.0:0.50 | 130 | 0.50 76 | massive cleavage* | |

TABLE 3-continued

Effect of Concentration
(Solvent/Substrate wt. % Ratio) & Nitrogen mixing
on Thermal Bromination (~75 mol % $Br_2$) of MMB in CB.

| Entry | MMB:CB | Temp (C.) | $Br_2$ rate & mol. % | Isolated acids (g) | Comments |
|---|---|---|---|---|---|

Starting material, MMB = 150 g (1.0 mol). Liquid $Br_2$ feed rate is in ml/min. Mixing rate 300 rpm in all entries unless noted otherwise. N2 refers to mixing bromine with nitrogen prior to reacting with the toluate esters.
*Cleavage to form solids refer to both starting ester and its benzyl bromide as stated in Table 1.

TABLE 4

Effect of Nitrogen mixing on Thermal Bromination (~75 mol % $Br_2$) under identical MMB/CB Concentrations (wt. ratios).

| Entry | MMB:CB | Temp (C.) | $Br_2$ rate & mol. % | Isolated acids (g) | Comments |
|---|---|---|---|---|---|
| 9. | 1.0:1.0 | 133–143 | 0.50 75 | 6.4 g | |
| 10. | 1.0:1.0 | 142–145 | 0.50 75 | 0.6 g | $N_2$ |

TABLE 4-continued

Effect of Nitrogen mixing on Thermal Bromination (~75 mol. % $Br_2$) under identical MMB/CB Concentrations (wt. ratios).

| Entry | MMB:CB | Temp (C.) | $Br_2$ rate & mol. % | Isolated acids (g) | Comments |
|---|---|---|---|---|---|
| 11. | 1.0:1.0 | 145 | 0.50  75 | No trace* | $N_2$, 400 rpm |

Starting material, MMB = 150 g (1.0 mol). Mixing rate 300 rpm in all entries unless noted otherwise. $N_2$ refers to mixing bromine with nitrogen prior to reacting with the toluate esters.
*This represents the optimum reaction conditions. Moderate bromine addition, fast mixing, and dilution by nitrogen (also rate acceleration) all lead to fast bromine consumption. Fast HBr removal and bromine concentration dilution by nitrogen helps speed the bromination reaction and minimize benzal byproduct formation (selectivity of benzyl to benzal ~12. With liquid bromine feed this ratio is reduced to ~9.5.

The results in Tables 2–4 indicate that efficient mixing of added bromine is an important factor in avoiding ester cleavage during thermal benzylic bromination. As seen from Table 3, when bromine is added to a highly concentrated ester solution, ester cleavage (a demethylation reaction) competes effectively with the halogenation process. With solutions of 1.5:1 ester/solvent weight ratios (entries 5–7) brominated at similar bromine addition rates, temperature, and conversion, ester cleavage occurred to a greater or lesser extent. The cleavage (demethylation) was less apparent when bromine was premixed with nitrogen (entry 5) and when the stirring rate was increased (entry 7). Ester cleavage (or solid acids formation) was extensive when the MMB concentration was the highest (ester/solvent ratio 1:0.5). Ester demethylation was massive (entry 8) and the solid formation in the reaction mixture was physically apparent (a slurry) even at 130° C. During experiments such as these, it was easy to judge how smooth the bromination reaction was proceeding by lack of dark bromine color and by the absence of any solid (slurry) formation. The results of Table 4 (entries 9–11) are from brominations carried out in a 1:1 solvent to MMB ester weight ratios. All were performed under similar conversion, bromine addition rates, and reaction temperatures. This solvent/substrate ratio (i.e., 50 wt. % ester solution) represents a preferred minimum solvent/ester ratio (or maximum ester concentration) for avoiding significant ester cleavage. As can be seen in Table 4, dilution of liquid bromine with nitrogen led to minimal solid formation (entry 10). Premixing the added bromine with nitrogen also leads to reaction rate acceleration. Combining nitrogen dilution and better mechanical stirring (entry 11) proved to be the best reaction conditions of this group of experimental runs: no acid formation (i.e., no ester cleavage) was detected by GC analysis of the crude reaction mixture.

EXAMPLE 5

Several brominations were conducted using ethyl 4-methylbenzoate and either chlorobenzene (CB) or ethylene dibromide (EDB) as the solvent. Table 5 summarizes the conditions used and results obtained.

TABLE 5

Effect of Concentration (Solvent/Substrate Weight Ratio) on Thermal Bromination (~60 mol % $Br_2$) of EMB in CB and EDB

| Entry | MMB:CB | Temp (C.) | $Br_2$ rate & mol. % | Isolated acids (g) | Comments |
|---|---|---|---|---|---|
| 1. | 1.0:2.8 | 139–142 | 0.50  61 | None | Sol = EDB |
| 2. | 1.0:1.0 | 145 | 0.50  63 | None | Sol = CB, 400 rpm |
| 3. | 1.0:1.52 | 138–146 | 0.50  62 | None | Sol = CB |

Sol: indicates reaction solvent. Liquid $Br_2$ feed rate is in ml/min via pump. Mixing rate 300 rpm in all entries unless noted otherwise.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for the direct preparation of a (1-haloalkyl) benzoic acid ester from an alkylbenzoic acid ester in which the alkyl group is a primary or secondary alkyl group and wherein the ester group (i) is devoid of non-aromatic unsaturation and (ii) if an aromatic group, is devoid of ring substitution that would undergo benzylic halogenation, said process comprising slowly feeding halogen continuously and/or intermittently to an agitated solution of said alkylbenzoic acid ester in a liquid halogen-containing solvent maintained at a thermal halogenation temperature such that when the alkyl group of the alkylbenzoic acid ester is a primary alkyl group the total amount of halogen fed does not exceed about 0.8 mole of halogen per mole of alkylbenzoic acid ester.

2. A process of claim 1 wherein the halogen is chlorine.

3. A process of claim 1 wherein the halogen is bromine.

4. A process of claim 3 wherein the bromine is fed as a solution in a liquid halogen-containing solvent.

5. A process of claim 3 wherein the bromine is fed as a vaporous mixture with at least one inert gas.

6. A process of claim 1 wherein the halogenation is conducted at one or more thermal halogenation temperatures in the range of about 110 to about 150° C.

7. A process of claim 1 wherein the alkyl group is a primary alkyl group.

8. A process of claim 7 wherein the halogen is bromine and wherein the halogenation is conducted at one or more thermal bromination temperatures in the range of about 110 to about 150° C.

9. A process for the direct preparation of a monohalomethylbenzoate ester from a toluic acid ester in which the ester group (i) is devoid of non-aromatic unsaturation and (ii) if an aromatic group, is devoid of ring substitution that would undergo benzylic halogenation, said process comprising slowly feeding halogen continuously and/or intermittently to an agitated solution of said toluic acid ester in a liquid halogen-containing solvent maintained at a thermal halogenation temperature such that the total amount of halogen fed does not exceed about 0.8 mole of halogen per mole of toluic acid ester.

10. A process of claim 9 wherein the toluic acid ester is a p-toluic acid ester in which the ester group has no more than about 12 carbon atoms.

11. A process of claim 9 wherein the toluic acid ester is methyl p-toluate or ethyl p-toluate.

12. A process for the direct preparation of a monobromomethylbenzoate ester from a toluic acid ester in which the ester group (i) is devoid of non-aromatic unsaturation and (ii) if an aromatic group is devoid of ring substitution that would undergo benzylic bromination, said process comprising slowly feeding bromine in increments continuously and/or intermittently to an agitated solution of said toluic acid ester in a liquid halogen-containing solvent maintained at a thermal bromination temperature, and controlling the reactant proportions such that the total amount of bromine fed does not exceed about 0.8 mole of bromine per mole of toluic acid ester.

13. A process of claim 12 wherein the toluic acid ester is a p-toluic acid ester in which the ester group has no more than about 12 carbon atoms.

14. A process of claim 12 wherein the bromination is conducted at one or more thermal bromination temperatures in the range of about 110 to about 150° C.

15. A process of claim 12 wherein the toluic acid ester is methyl p-toluate or ethyl p-toluate.

16. A process of claim 15 wherein the bromination is conducted at one or more thermal bromination temperatures in the range of about 110 to about 150° C.

17. A process of claim 16 wherein the solvent is chlorobenzene or ethylene dibromide.

18. A process of claim 16 wherein the bromine is fed as a solution in a liquid halogen-containing solvent.

19. A process of claim 16 wherein the bromine is fed as a vaporous mixture with at least one inert gas.

20. A process of claim 12 wherein the toluic acid ester is methyl p-toluate or ethyl p-toluate, wherein the bromine is fed as a vaporous mixture with at least one inert gas, wherein the solvent is chlorobenzene or ethylene dibromide, and wherein the bromination is conducted at one or more thermal bromination temperatures in the range of about 130 to about 150° C.

21. A process for the direct preparation of a (1,1-dihaloalkyl)benzoic acid ester from an alkylbenzoic acid ester in which the alkyl group is a primary alkyl group having at least two carbon atoms and wherein the ester group (i) is devoid of non-aromatic unsaturation and (ii) if an aromatic group, is devoid of ring substitution that would undergo benzylic halogenation, said process comprising slowly feeding halogen continuously and/or intermittently to an agitated solution of said alkylbenzoic acid ester in a liquid halogen-containing solvent maintained at a thermal halogenation temperature such that the total amount of halogen fed is in excess of 1 mole of halogen per mole of alkylbenzoic acid ester.

22. A process of claim 21 wherein the halogen is bromine.

23. A process of claim 22 wherein the bromine is fed as a solution in a liquid halogen-containing solvent.

24. A process of claim 22 wherein the bromine is fed as a vaporous mixture with at least one inert gas.

25. A process of claim 21 wherein the halogenation is conducted at one or more thermal halogenation temperatures in the range of about 110 to about 150° C.

26. A process of claim 21 wherein the halogen is bromine and wherein the bromination is conducted at one or more thermal bromination temperatures in the range of about 135 to about 145° C.

27. A process of claim 21 wherein the alkylbenzoic acid ester is a p-alkylbenzoic acid ester in which the esterifying group contains no more than about 12 carbon atoms, wherein the halogen is bromine, and wherein the bromination is conducted at one or more thermal bromination temperatures in the range of about 110 to about 150° C.

28. A process of claim 27 wherein the p-alkylbenzoic acid ester is methyl p-toluate or ethyl p-toluate.

29. A process for the direct preparation of a (1,1-dihalomethyl)benzoic acid ester from a toluic acid ester wherein the ester group (i) is devoid of non-aromatic unsaturation and (ii) if an aromatic group, is devoid of ring substitution that would undergo benzylic halogenation, said process comprising slowly feeding halogen continuously and/or intermittently to an agitated solution of said toluic acid ester in a liquid halogen-containing solvent maintained at a thermal halogenation temperature such that the total amount of halogen fed is in the range of more than 1 mole and no more than about 1.8 moles of halogen per mole of toluic acid ester.

30. A process of claim 29 wherein the toluic acid ester is methyl p-toluate or ethyl p-toluate, wherein the halogen is bromine, and wherein the bromination is performed within the temperature range of about 110 to about 150° C.

* * * * *